US00RE38630E1

(19) United States
(12) Reissued Patent
Lazzara et al.

(10) Patent Number: US RE38,630 E
(45) Date of Reissued Patent: Oct. 19, 2004

(54) METHODS AND MEANS FOR DENTAL BONE PROFILING

(75) Inventors: Richard J. Lazzara, Lake Worth, FL (US); Keith D. Beaty, Jupiter, FL (US); Stuart Graves, Burke, VA (US)

(73) Assignee: Implant Innovations, Inc., Palm Beach Gardens, FL (US)

(21) Appl. No.: 09/776,145

(22) Filed: Feb. 2, 2001

Related U.S. Patent Documents

Reissue of:
(64) Patent No.: 5,868,572
Issued: Feb. 9, 1999
Appl. No.: 08/821,917
Filed: Mar. 18, 1997

U.S. Applications:

(63) Continuation of application No. 08/498,188, filed on Jul. 5, 1995, now abandoned.

(51) Int. Cl.[7] ..... A61C 8/00; A61C 3/02
(52) U.S. Cl. ..... 433/173; 433/165
(58) Field of Search ..... 433/165, 166, 433/172, 173, 174, 175, 176; 407/54, 57, 61; 606/180, 79, 80

(56) References Cited

U.S. PATENT DOCUMENTS

| | | | | |
|---|---|---|---|---|
| 1,123,730 A | | 1/1915 | Greenfield | |
| 1,200,921 A | | 10/1916 | Chester | |
| 1,333,388 A | | 3/1920 | Chester | |
| 1,827,511 A | | 10/1931 | Evans | |
| 3,058,218 A | | 10/1962 | Kleesattel et al. | |
| 3,971,135 A | | 7/1976 | Leu | |
| 4,179,810 A | | 12/1979 | Kirsch | 433/75 |
| 4,187,609 A | | 2/1980 | Edelman | 433/176 |
| 4,229,169 A | | 10/1980 | Smith et al. | 433/174 |
| 4,297,059 A | | 10/1981 | Miyanaga | 408/202 |
| 4,352,610 A | | 10/1982 | Yankovoy et al. | 408/206 |
| 4,465,463 A | | 8/1984 | Olde | 433/141 |
| 4,560,308 A | | 12/1985 | Deller | 407/53 |
| 4,741,651 A | | 5/1988 | Despres | 408/209 |
| 4,744,754 A | | 5/1988 | Ross | 433/173 |
| 4,854,872 A | | 8/1989 | Detsch | 433/173 |
| 4,976,739 A | | 12/1990 | Duthie, Jr. | 623/16 |
| 5,071,351 A | | 12/1991 | Green, Jr. et al. | 433/173 |
| 5,078,605 A | | 1/1992 | Sutter et al. | 433/165 |
| 5,169,308 A | | 12/1992 | Kvist | 433/173 |
| 5,180,303 A | | 1/1993 | Hornburg et al. | 433/173 |
| 5,201,656 A | | 4/1993 | Sicurelli, Jr. | 433/166 |
| 5,254,005 A | | 10/1993 | Zuest | 433/173 |
| 5,338,196 A | | 8/1994 | Beaty et al. | 433/172 |
| 5,762,499 A | * | 6/1998 | Dard et al. | 433/173 |
| 5,782,636 A | * | 7/1998 | Armstrong et al. | 433/173 |

FOREIGN PATENT DOCUMENTS

| | | | |
|---|---|---|---|
| DE | 680464 | 8/1939 | |
| EP | 0 126 624 | 11/1984 | A61C/8/00 |
| FR | 1021597 | 12/1952 | |
| GB | 10311 | of 1901 | |
| GB | 1 401 862 | 8/1975 | A61C/13/30 |
| JP | 6-125923 | 5/1994 | A61C/8/00 |
| RU | 1659037 A1 | 6/1991 | |
| WO | WO 92/22260 | 12/1992 | A61C/8/00 |

OTHER PUBLICATIONS

"Nobelpharma Special Products Catalog," copyright 1995.
"Product News Bone Mill and Guide Provide Elegant Solution," p. 7, *Nobelpharma News*, Issue No. 2/94, 1994.

(List continued on next page.)

*Primary Examiner*—Cary E. O'Connor
(74) *Attorney, Agent, or Firm*—Jenkens & Gilchrist

(57) ABSTRACT

A bone mill for preparing the second-stage opening in crestal bone surrounding the gingival surface of a dental implant in a jawbone is tubular in form and has teeth with a negative rake on an end surface and the adjacent side surface for forming a shaped opening to the implant. The side surface of the mill near the end surface is tapered to the desired shape of the opening. A guide pin fixed in the implant mates with an opening in the bone mill to center the mill relative to the implant.

68 Claims, 5 Drawing Sheets

OTHER PUBLICATIONS

"Nobelpharma Product Catalog," copyright 1993, 1994.
"Branemark System® Price List," effective May 15, 1995.
Adell, R., et al., *A 15–Year Study of Osseointegrated Implants In The Treatment Of The Edentulous Jaw*, Int. J. Oral Surg., vol. 10, pp. 387–416 (1981).
Price List and Ordering Information, *The Spline Dental Implant System*, Calcitek, 2 pages (Sep. 1995).
Product Catalog, Minimatic Implant Systems, 2 pages (May 15, 1994).
USA Product Catalog, *ITI® Dental Implant System*, Straumann Dental, 2 pages (no date).
Implant Innovations, Inc., "Surgical Price List" with drawing of bone profiler and guide, May 1995.
Busch & Co., Bur Advertisement, Journal of the American Dental Association, Aug. 1968, vol. 77, No. 2, p. 435.
Reading's Specification, Jun. 1882, No. 2893.
Busch & Co., Bur Advertisement.
Nobelpharma AB, Special Products Catalog, "Special Instruments for Abutment Connection".

* cited by examiner

METHODS AND MEANS FOR DENTAL BONE PROFILING

Matter enclosed in heavy brackets [ ] appears in the original patent but forms no part of this reissue specification; matter printed in italics indicates the additions made by reissue.

This application is a continuation of application Ser. No. 08/498,188 filed Jul. 5, 1995 now abandoned.

This invention relates generally to the field of dental implants and their use, more particularly to the preparation of crestal bone surrounding an implant at the site of installation for receiving a dental restoration on the implant.

BACKGROUND OF THE INVENTION

U.S. Pat. No. 5,338,196 (which is owned by the Assignee of the present application) teaches, among other things, a second-stage healing abutment for forming and preserving in the mucosa above a dental implant a transmucosal opening large enough to receive an artificial tooth which faithfully replicates a natural tooth being restored. This opening expands in size from the implant to the outer surface of the overlying gingiva, where the opening has width approximating that of the lost natural tooth being replaced, where it emerged from the gums. During the first stage of dental implantation, however, when the implant with its cover screw is left unloaded in the jawbone for a time interval while osseointegration proceeds, the crestal cortical bone tends to grow over the periphery of the cover screw, and this overgrowth must be removed at the beginning of the second stage, if only to permit the cover screw to be removed from the implant. Removing this bone overgrowth is now done by hand. This practice is tedious and imprecise, and potentially harmful to the patient.

GENERAL NATURE OF THE INVENTION

According to the present invention an expanding hole is formed in the crestal bone surrounding the gingival surface of the implant, the shape of which hole preferably matches and mates with the expanding hole in the overlying gingiva. In this preferred embodiment of the invention there is presented to the restoring dentist a continuous tapered hole from the gingival surface through the gingiva and the underlying crestal bone to the surface of the implant, through which to instal an artificial tooth on the implant. The present invention further provides improved means for forming a desired hole in the crestal bone accurately and precisely shaped and positioned with relation to the implant, and without damaging the bone or the implant surface. More particularly, the present invention teaches a new bone mill using teeth with a negative rake to provide a passive cutting action which minimizes damage to the bone and to the surface of the implant, together with a method of using it which emphasizes low speed turning. The present invention provide means to limit the progress of the bone mill toward the implant surface, which further safeguards the surface of the implant.

The present invention improves and enhances the utility of the second-stage healing abutment which is taught in the '196 patent, which is now provided with improved access to the implant and can be seated with assured precision on the implant. Since the process of making an artificial tooth begins with the healing abutment, these benefits flow through to the artificial tooth that will ultimately be installed on the implant.

DETAILED DESCRIPTION OF THE DRAWINGS

Figure 1:
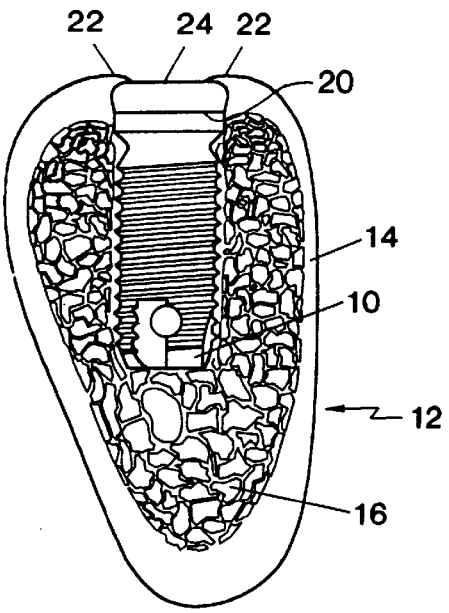
FIG. 1 is a transverse section of jawbone with a dental implant and cover screw installed, in the first stage of osseointegration.
Figure 2:
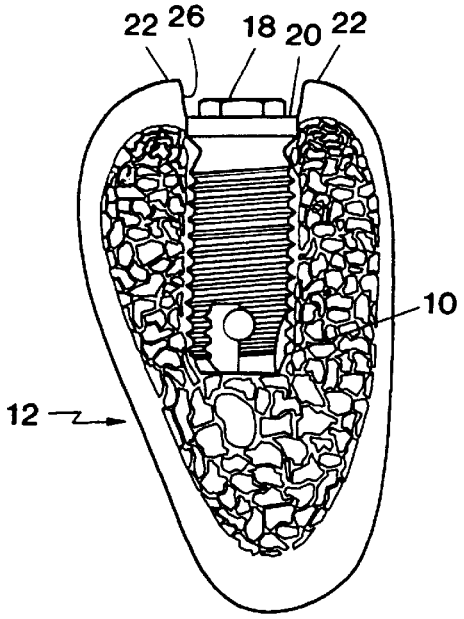
FIG. 2 is a similar section with the cover screw removed showing crestal bone removed to give access to the cover screw, as done heretofore.

FIGS. 1 and 2 illustrate the background situation described above. In FIG. 1 the implant 10 is installed in jawbone 12, composed of cortical bone 14 surrounding cancellous bone 16. The supragingival (top) surface 20 of the implant is located to penetrate the crestal cortical bone 22. A cover screw 24, placed on the implant to seal its interior receiving bore (not shown) prior to starting the first stage healing process (osseointegration) lies within ther opening through the crestal bone. At the end of the first stage, when the overlying gum tissue (not shown) is opened to access the cover screw the dentist will usually find that the crestal bone 22 has grown over the cover screw, as is shown in FIG. 1, and must be removed, as by chipping it away, before the cover screw can be removed from the implant. The result of this initial procedure is shown in FIG. 2. A roughly round, somewhat tubular opening 26 is produced, giving access to the top surface 20 and to the non-rotational fitting 18 which may be an integral part of the implant.

Figure 3:
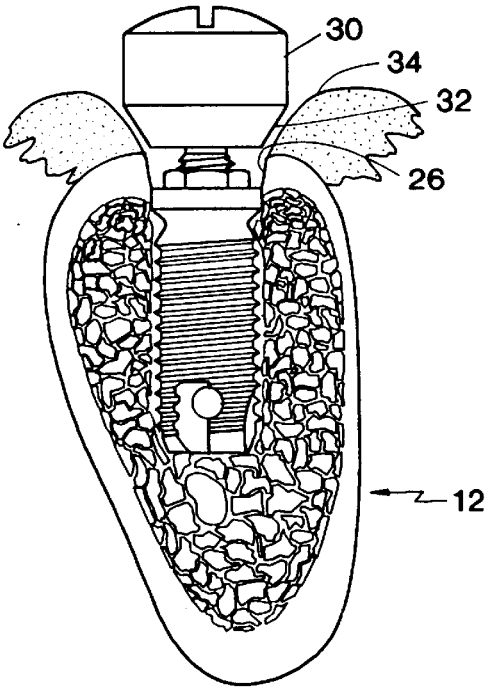
FIG. 3 is a section similar to FIG. 2 showing a healing abutment according to the '196 patent being fitted to the implant as prepared in FIG. 2.
Figure 4:
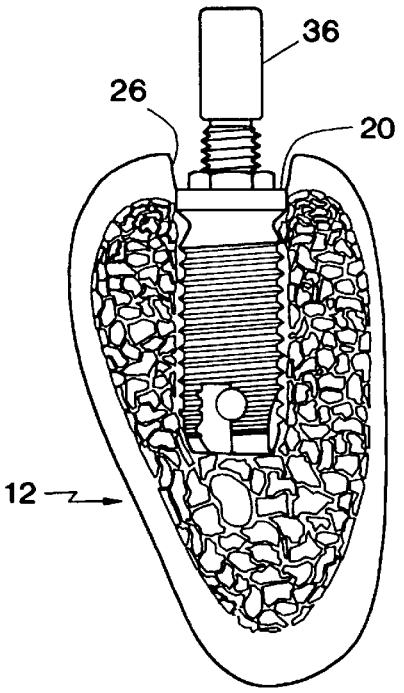
FIG. 4 is a section similar to FIG. 2 showing a guide pin according to the present invention being fitted to the implant.

In the circumstances of this background (prior-art) situation an attempt to fit to the implant a second-stage healing abutment according to the '196 patent may encounter difficulty, as is illustrated in FIG. 3. The healing abutment 30 has a tapered section 32 that is shaped for the purpose of forming in the overlying mucosa 34 a transmucosal opening as is described in the '196 patent. The opening 26 must be altered to provide passage for the abutment to the supragingival surface 20 of the implant. This might be done by further chipping away crestal bone, resulting in most cases in a larger rough opening in the crestal bone 22. The present invention provides a better way, starting with the fitting of a guide-pin 36 to the implant, as is shown in FIG. 4.

Figure 5:
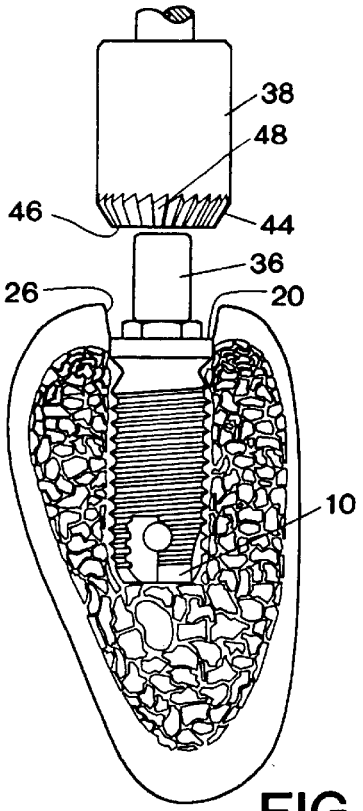
FIG. 5 is a section similar to FIG. 4 showing the guide pin in place and a bone mill according to the invention being fitted to it.
Figure 6:
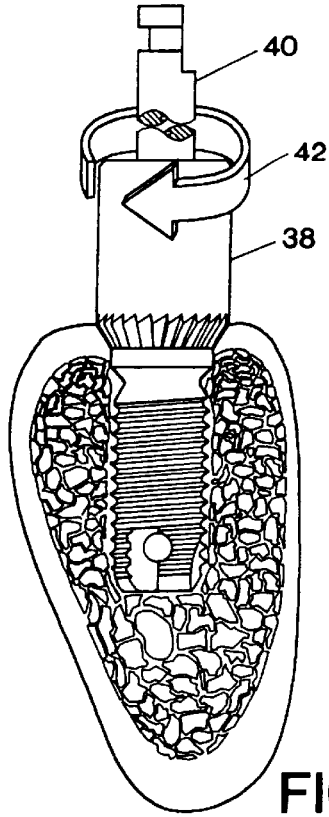
FIG. 6 is a section similar to FIG. 5 showing the bone mill being turned to for a tapered opening in the crestal bone above the implant.
Figure 7:
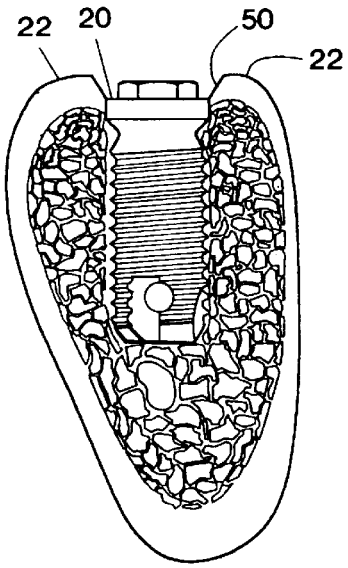
FIG. 7 is a section similar to FIG. 2 showing the tapered opening formed by the present invention in the crestal bone.
Figure 8:
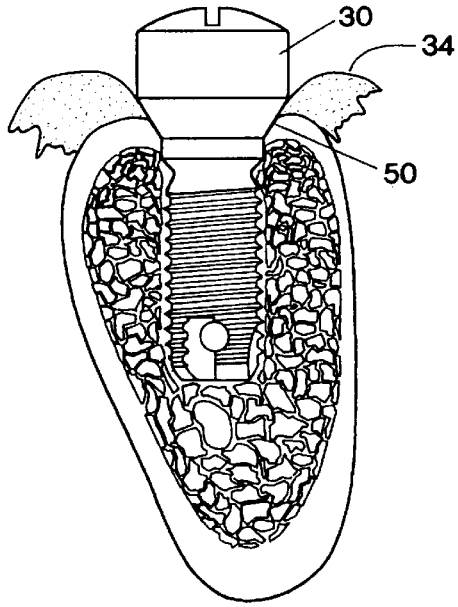
FIG. 8 is a section similar to FIG. 3 showing the healing abutment seated on the implant through the tapered opening of the present invention.

A bone mill 38 according to the invention is fitted over the guide-pin 36, which centers the bone mill on the implant 10 and guides it to the crestal bone opening 26 and the surface 20 of the implant., as is shown in FIGS. 5 and 6. The bone mill may be fitted with a driving stem 40 of a known design for connecting it to a dental driving tool (not shown). An arrow 42 indicates the driving direction, The bone mill (to be described in greater detail with reference to FIGS. 9 and 10) is fitted with cutting teeth 48 on a tapered side 44 and on its end 46 confronting the surface 22. With this bone mill an accurately centered and shaped tapered hole 50 is formed in the crestal bone 22, as is shown in FIG. 7. The angle of taper of the bone mill surface 44 is chosen substantially to match to angle of taper of the tapered surface 32 of the healing abutment 30, so that the healing abutment fits snugly into the tapered hole 50 and seats on the implant top surface 20. Desirably, the taper of the hole 50 in the crestal bone 22 and the taper of the hole through the gum tissue 34 may be on the same angle, so that the present invention used with the invention of the '196 patent will produce in essence a single continuous tapered hole from the outer gingival surface through the mucosa and the crestal bone to the top surface 20 of the implant.

Figure 9:
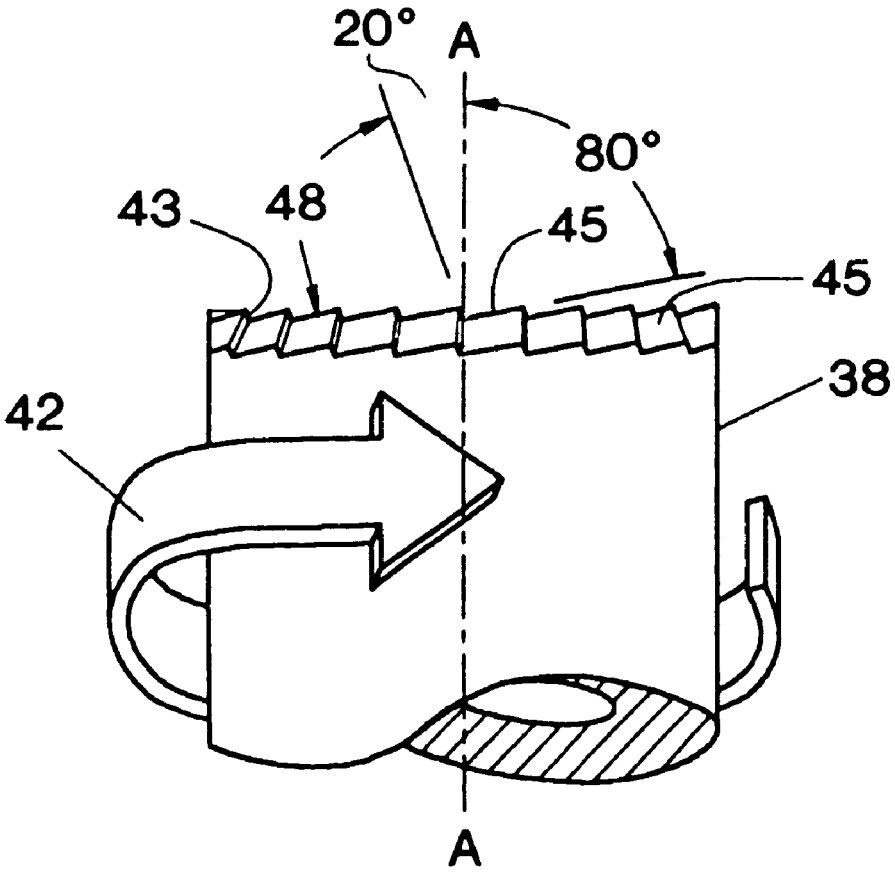
FIG. 9 is a partial schematic view of the bone mill showing locations of its teeth.

FIG. 9 is a partial side view of the bone mill 38 showing the negative rake of the cutting teeth 48 relative to the turning direction indicated by the arrow 42. As is here illustrated the shorter approaching face 43 has a negative rake of 20 degrees measured from the turning axis A—A. The longer receding face 45 has an angle of 80 degrees measured from the same axis. The angle between the two faces of a tooth is thus 100 degrees. The teeth 48 when turned at a slow speed of about 1,000 to 1,500 rpm will gently abrade the crestal bone 22 and will not dig into or damage the surface 20 of the implant.

Figure 10:
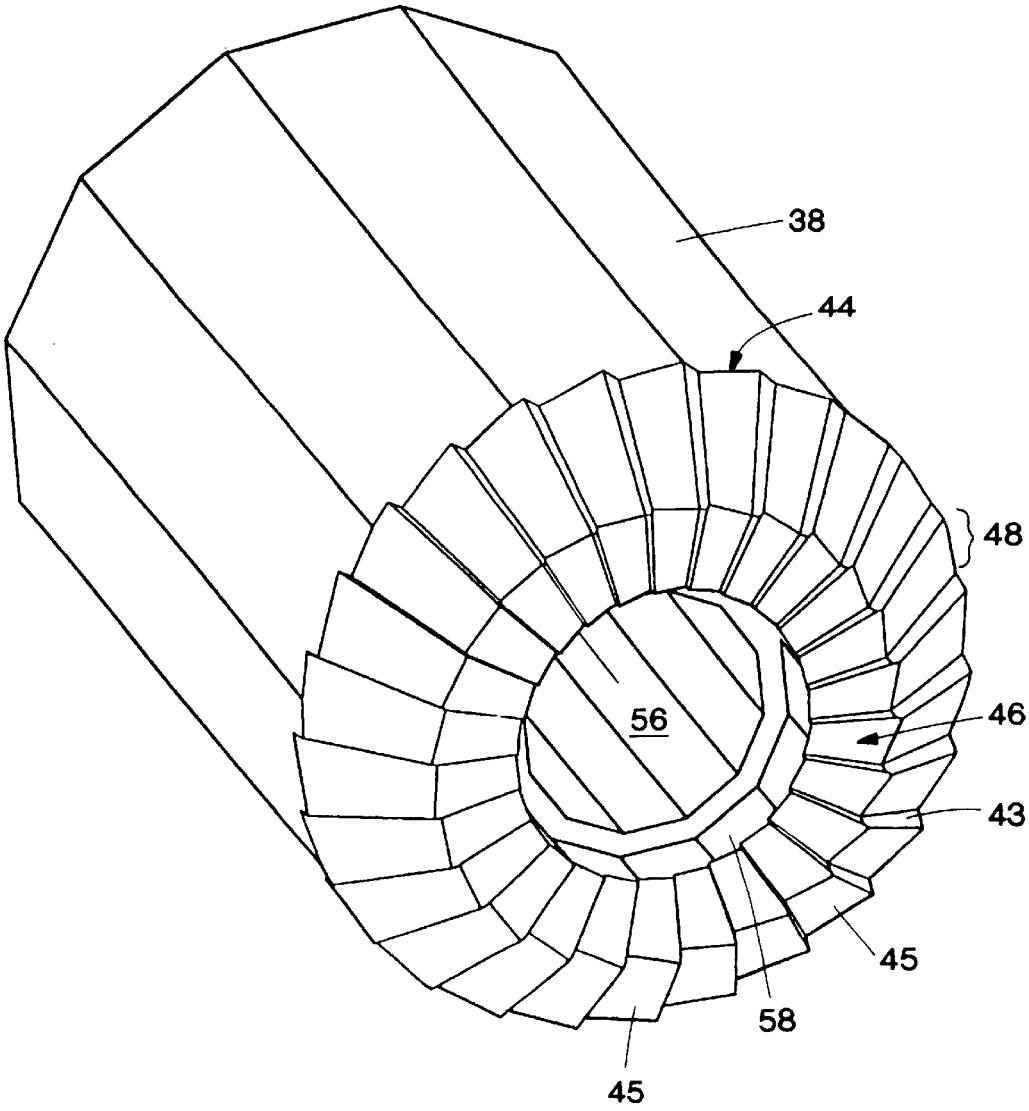
FIG. 10 is an enlarged isometric schematic view of the bone mill.

FIG. 10 is a greatly magnified isometric schematic view of the bone mill 42 showing the locations of the cutting teeth on the tapered side surface 44 and on the end surface 46. The angles of the teeth are the same on both surfaces.

Figure 11:
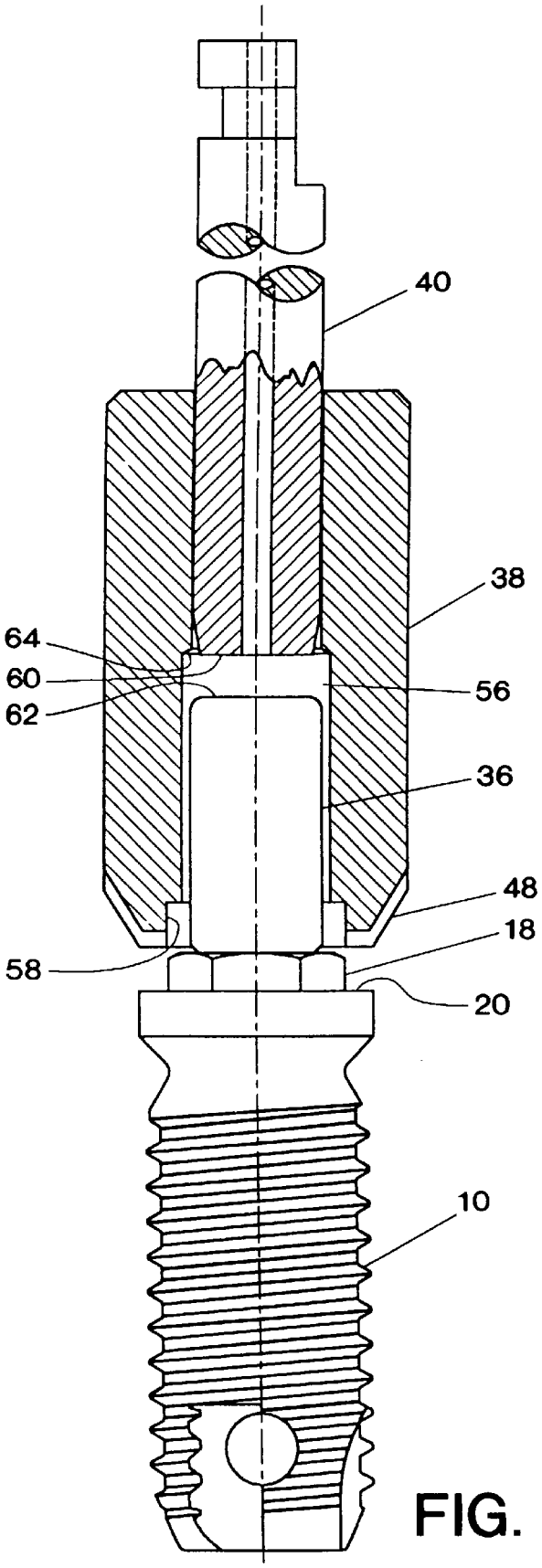
FIG. 11 is a longitudinal section through the bone mill with the guide pin in place.

FIG. 11 is a longitudinal side view of an implant 10, guide pin 36 and bone mill 42 as they would be assembled to do the work of the invention. The bone mill is generally tubular in shape, and the driving stem partially fills its interior bore 56. The remainder of the bore, which opens through the end 46, receives the guide pin 36. A round recess 58 in the end 46 serves to receive the non-rotational fitting 18 of the implant, without engaging it, so that the bone mill is freely rotatable on the implant. The top surface 62 of the guide pin, inside the bore 56 confronts a stop 60 across the bore when the milling teeth 48 meet the implant surface 20, for limiting the advance of the bone mill with relation to the implant surface. The stop 60 can be provided by the driving stem 40, as shown, or if desired by a separate shoulder 64 within the bore 56.

We claim:

1. A method of preparing a dental implant which is fixed in a living jawbone with its restoration-receiving surface surrounded by crestal bone comprising the steps of:

forming in said crestal bone [a tapered] *an* opening the [narrower] *first* end of which is substantially centered on said surface and the [wider] *second* end of which opens through said crestal bone, and fitting to said implant through said opening a healing member having a [tapered] contour in said opening which substantially matches [the tapered] *a* contour of said opening.

2. A method according to claim 1 in which said opening is formed with a bone mill.

3. A method according to claim 2 in which said opening is formed with a bone mill turned at a low speed so as not to injure said bone.

4. A method according to claim 2 in which said opening is formed with a bone mill having teeth with a negative rake for gently abrading said bone and minimizing potential damage to said surface.

5. A method according to claim 2 including the steps of fitting to said implant a guide for said bone mill, fitting said bone mill rotatably to said guide, and rotating said bone mill around said guide to form said opening.

6. A method according to claim 5 including the step of using said guide to limit the advance of said bone mill relative to said surface.

7. A bone mill having a substantially cylindrical outer shape comprising teeth with a negative rake on an end and an adjacent side.

8. A bone mill according to claim 7 of tubular form.

9. A bone mill according to claim 7 in which said side is tapered toward said end.

10. A bone mill according to claim 7 including means to rotate said mill around its tubular axis.

11. A bone mill according to claim 10 in combination with a guide fittable within said mill through said end for fixing the position of said axis relative to a work site.

12. A combination according to claim 11 including means to limit advance of said bone mill toward said work site.

13. A bone mill according to claim 10 in combination with guide means for fixing the position of said axis relative to a work site.

14. A method of preparing a dental implant which is fixed in a living jawbone with its restoration-receiving surface surrounded by crestal bone overlaid with mucosa comprising the steps of forming in said crestal bone a first tapered opening the narrower end of which is substantially centered on said surface and the wider end of which opens through said crestal bone to said mucosa, and forming through said mucosa to said wider end a second tapered opening the narrower end of which has substantially the same width as said wider end of said first opening and the wider end of which opens through the outer surface of said mucosa.

15. A method according to claim 14 in which said first and second openings have substantially the same angle of taper.

16. A method according to claim 14 in which said second opening is formed with a healing member having a surface shaped with a tapered contour which substantially matches the tapered contour of said first opening, comprising the steps of fitting said healing member to said implant through said first opening, and forming said second opening with a portion of said surface extending out of said first opening.

17. A method according to claim 14 in which said first opening is formed with a bone mill.

18. A method according to claim 17 including the steps of fitting to said implant a guide for said bone mill, fitting said bone mill rotatably to said guide, and rotating said bone mill around said guide to form said opening.

19. A method according to claim 18 including the step of using said guide to limit the advance of said bone mill with relation to said implant surface.

20. A method according to claim 14 in which said first opening is formed with a bone mill turned at low speed of about 1,000 to about 1,500 r.p.m., so as not to injure said bone.

21. A method according to claim 14 in which said first opening is formed with a bone mill having teeth with a negative rake.

22. In combination a dental implant adapted to be installed in a jawbone with an end surface of said implant exposed through an opening in the crestal bone, and a bone mill for shaping said opening comprising a substantially cylindrical body bearing on an end and an adjacent side teeth with a negative rake.

23. The combination according to claim 22 wherein said bone mill is of tubular form.

24. A combination according to claim 23 in which said side is tapered toward said end.

25. A combination according to claim 23 including means to rotate said mill around its tubular axis.

26. A combination according to claim 25 in combination with a guide telescopically fittable within said mill through said end for fixing the position of said axis relative to said implant.

27. A combination according to claim 26 including means to limit the advance of said bone mill with relation to said implant surface.

28. A combination according to claim 26 in which said implant is substantially cylindrical, said bone mill is at least partially tubular with a substantially cylindrical passage opening through one end of said bone mill, said guide is a pin fixed on the cylinder axis of said implant, said bone mill passage fits telescopically over said pin, and said means to operate said bone mill turns said bone mill on said axis.

29. A combination according to claim 28 in which said passage includes a stop to limit penetration of said pin into said passage, for limiting the advance of said bone mill with reference to said end surface of said implant.

30. A combination according to claim 28 in which said bone mill has teeth on said one end and on the portion of its outer side surface adjacent said one end.

31. A combination according to claim 30 in which said portion of said outer surface is tapered toward said one end.

32. A combination according to claim 30 in which said teeth have a negative rake.

33. A combination according to claim 32 in which said negative rake is about 20 degrees.

34. In combination a dental implant adapted to be installed in the bone of a dental arch with an end surface of said implant exposed through an opening in the crestal bone, a bone mill having teeth on an end and an adjacent side for shaping said opening in width and depth, *said bone mill having an exterior profile that is tapered to produce a tapered shape of said opening* and guide means for locating said bone mill relative to said implant and said opening.

35. A combination according to claim 34 including means to operate said bone mill relative to said implant for shaping said opening.

*36. The method according to claim 1, wherein said contour of said opening in said crestal bone is tapered and said contour of said healing member is tapered.*

*37. The method according to claim 36, wherein said tapered contour of said opening substantially matches said tapered contour of said healing member.*

*38. A method of preparing bone adjacent to a restoration-receiving surface of a dental implant, said dental implant receiving a healing abutment to form gingiva overlying said bone, comprising:*

*forming an opening in said bone with a bone mill, said opening having a contour substantially corresponding to an exterior profile of said bone mill, said exterior profile having a shape that substantially matches the shape of said healing abutment.*

*39. The method according to claim 38, wherein said forming includes attaching a guide to said dental implant, and guiding said bone mill over said guide.*

*40. The method according to claim 38, wherein said exterior profile is tapered.*

*41. The method according to claim 38, wherein said bone mill includes cutting teeth having a negative rake.*

*42. The method according to claim 38, wherein said forming includes rotating said bone mill at a speed of between about 1000 rpm and 1500 rpm.*

*43. A set of components for forming an opening in bone adjacent to a restoration-receiving surface of a dental implant, comprising:*

*a bone mill including a hole at one end and cutting teeth at said end, said bone mill has an exterior profile that is tapered to produce a tapered shape of said opening; and*

*a guide attachable to said dental implant, said guide fitting within said hole of said bone mill for registering said bone mill relative to said implant.*

*44. The set of components of claim 43, wherein said bone mill further includes cutting teeth located on a side surface of said bone mill.*

*45. The set of components of claim 43, further in combination with a healing abutment for shaping gingiva overlying said bone, said bone mill having an exterior profile that substantially matches the shape of said healing abutment.*

*46. The set of components of claim 45, wherein said exterior profile is tapered.*

*47. The set of components of claim 45, wherein said bone mill and said healing abutment form a continuous tapered hole through said gingiva and said bone.*

*48. The set of components of claim 43, wherein said hole is partially defined by a surface transverse to a central axis of said bone mill, said surface for engaging said guide to limit the movement of said bone mill relative to said implant.*

*49. The set of components of claim 43, wherein said cutting teeth have a negative rake.*

*50. The set of components of claim 49, wherein said bone mill has an exterior profile that is tapered.*

*51. The set of components of claim 43, wherein said bone mill is power driven.*

*52. A set of dental components, comprising:*

*a dental implant for installation in living bone having a restoration-receiving surface exposed through an opening in said bone; and*

*a bone mill having teeth with a negative rake on an end, said bone mill for shaping said opening in said bone adjacent to said restoration-receiving surface of said dental implant.*

*53. The set of components of claim 52, further including a guide for attachment to said dental implant, said bone mill having a hole for receiving said guide to register said bone mill on said implant.*

*54. The set of components of claim 53, wherein said hole is partially defined by a surface transverse to an axis of said bone mill, said surface for engaging said guide to limit the movement of said bone mill relative to said implant.*

*55. The set of components of claim 52, in combination with a healing member having a contour that substantially matches a contour of said bone mill.*

*56. The set of components of claim 55, wherein said contour of said bone mill is tapered and said contour of said healing member is tapered, said bone mill and said healing member forming a continuous tapered hole through gingiva and said bone.*

*57. A set of components for forming an opening in bone adjacent to a restoration-receiving surface of a dental implant, comprising:*

*a bone milling device including cutting teeth at a lower portion thereof, said bone milling device including a guide for engaging said dental implant and registering said bone milling device relative to said implant; and*

*a healing abutment for shaping gingiva overlying said bone, said healing abutment having a shape that substantially matches an exterior profile of said bone milling device.*

*58. The set of components of claim 57, wherein said guide is adapted to center said bone milling device relative to said surface of said implant.*

*59. The set of components of claim 57, wherein said guide is separate from said bone milling device.*

*60. The set of components of claim 57, wherein said exterior profile of said bone milling device is tapered.*

*61. The set of components of claim 57, wherein said healing abutment has a surface which is tapered.*

*62. The set of components of claim 57, wherein said bone milling device is power driven.*

*63. A set of components for forming a tapered opening in bone adjacent to a restoration-receiving surface of a dental implant, comprising:*

*a bone mill having a lower end and a tapered side surface that tapers outwardly from said lower end, said tapered side surface having cutting teeth for producing said tapered opening; and*

*a guide for engaging said dental implant and registering said bone mill relative to said implant.*

*64. The set of components of claim 63, wherein said guide and said bone mill are separate from one another.*

*65. The set of components of claim 63, wherein said guide is adapted to fit within a threaded bore of said implant.*

*66. The set of components of claim 65, wherein said guide is threaded.*

*67. The set of components of claim 63, wherein said guide is adapted to fit snugly within a bore of said implant.*

*68. The set of components of claim 63, wherein said bone mill is power driven.*

* * * * *